United States Patent
Hansson

(10) Patent No.: US 7,850,699 B2
(45) Date of Patent: Dec. 14, 2010

(54) DEVICE FOR EXTRACTION OF PINS AT FIXATION MEANS FOR FIXATION OF BONE FRAGMENTS AT BONE FRACTURES

(76) Inventor: Henrik Hansson, S-590 77, Vreta Kloster (SE)

( * ) Notice: Subject to any disclaimer, the term of this patent is extended or adjusted under 35 U.S.C. 154(b) by 38 days.

(21) Appl. No.: 10/509,606

(22) PCT Filed: Apr. 7, 2003

(86) PCT No.: PCT/SE03/00558

§ 371 (c)(1),
(2), (4) Date: Sep. 27, 2004

(87) PCT Pub. No.: WO03/086214

PCT Pub. Date: Oct. 23, 2003

(65) Prior Publication Data

US 2005/0149051 A1    Jul. 7, 2005

(30) Foreign Application Priority Data

Apr. 9, 2002    (SE)    .................................... 0201058

(51) Int. Cl.
*A61B 17/58* (2006.01)
(52) U.S. Cl. ........................ 606/104; 606/99
(58) Field of Classification Search .................. 606/73, 606/86, 96, 99, 104, 97, 98
See application file for complete search history.

(56) References Cited

U.S. PATENT DOCUMENTS

| | | | | |
|---|---|---|---|---|
| 2,243,717 A | * | 5/1941 | de Godoy Moreira | 606/65 |
| 2,631,584 A | * | 3/1953 | Purificato | 606/68 |
| 3,497,953 A | * | 3/1970 | Weissman | 433/173 |
| 4,237,875 A | * | 12/1980 | Termanini | 606/63 |
| 4,498,468 A | * | 2/1985 | Hansson | 606/68 |
| 4,530,355 A | * | 7/1985 | Griggs | 606/105 |
| 5,084,053 A | | 1/1992 | Ender | |
| 5,571,102 A | * | 11/1996 | Cavagna et al. | 606/250 |
| 5,707,373 A | * | 1/1998 | Sevrain et al. | 606/916 |
| 5,810,820 A | | 9/1998 | Santori et al. | |
| 6,053,653 A | * | 4/2000 | Tanaka et al. | 403/282 |
| 6,524,238 B2 | * | 2/2003 | Velikaris et al. | 600/213 |
| 6,592,587 B1 | * | 7/2003 | Roger | 606/73 |
| 2001/0056283 A1 | * | 12/2001 | Carter et al. | 606/148 |

FOREIGN PATENT DOCUMENTS

| | | |
|---|---|---|
| DE | 24 04 441 A1 | 7/1975 |
| EP | 0 425 472 B1 | 5/1991 |
| FR | 2 668 920 A1 | 5/1992 |
| JP | 3-218743 | 9/1991 |
| WO | WO 02/11632 A1 | 2/2002 |

* cited by examiner

*Primary Examiner*—Thomas C Barrett
*Assistant Examiner*—Michael T Schaper
(74) *Attorney, Agent, or Firm*—Tarolli, Sundheim, Covell & Tummino LLP

(57) ABSTRACT

A device for extraction of pins of fixation means for fixation of bone fragments at bone fractures is adapted to pull a pin (7) of the fixation means in a backwards direction relative to a sleeve (6) of the fixation means in order to withdraw a front part (11) of the pin (7) from bone material of one of the bone fragments (3, 4) and into the sleeve (6). The extraction device (1) includes members (12, 13, and 14) which are provided to draw or pull the pin (7) backwards relative to the sleeve (6) without thereby subjecting the pin (7) to torsional forces in relation thereto.

18 Claims, 5 Drawing Sheets

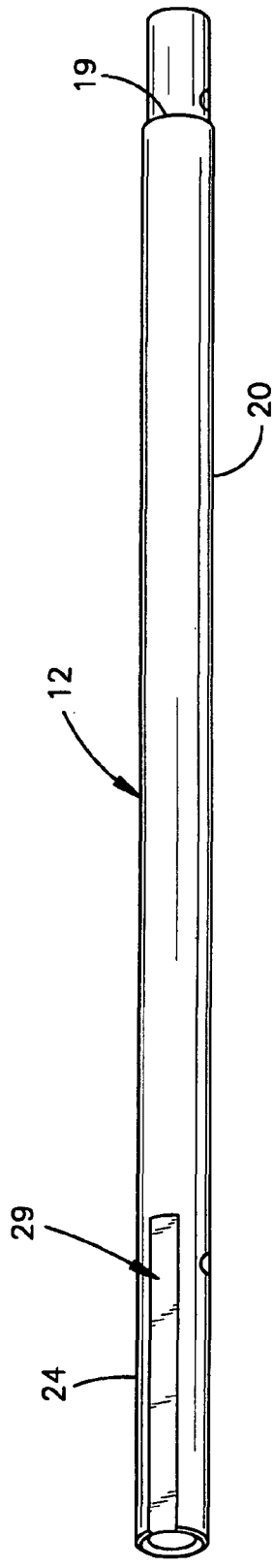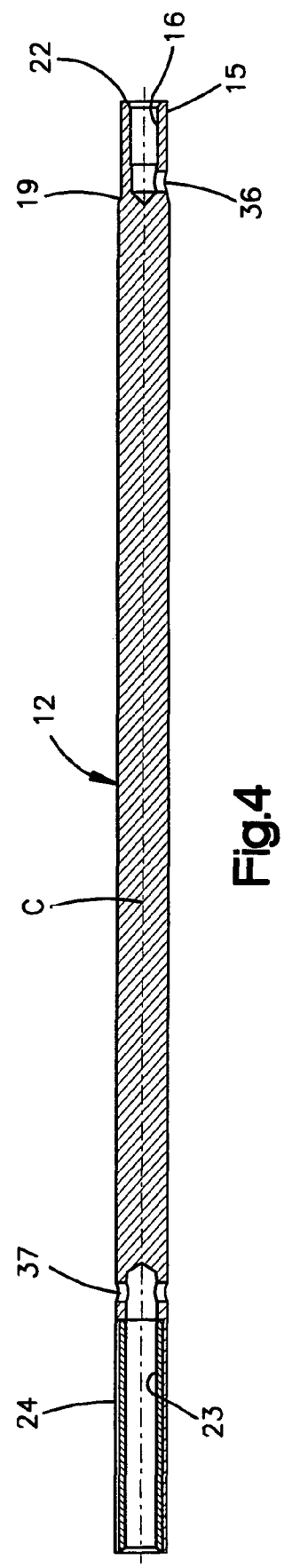

DEVICE FOR EXTRACTION OF PINS AT FIXATION MEANS FOR FIXATION OF BONE FRAGMENTS AT BONE FRACTURES

TECHNICAL FIELD

The present invention relates to a device for extraction of pins of fixation means for fixation of bone fragments at bone fractures. The fixation means includes a sleeve and at least one pin provided in said sleeve. The sleeve has at a front end portion at least one opening in a longitudinal side thereof. A front part of the pin extends, when it is located in an operating position, out of the sleeve through the opening and engages bone material of one of the bone fragments. The extraction device is adapted to pull the pin in a backwards direction relative to the sleeve in order to withdraw the front part of the pin from bone material of one of the bone fragments and into the sleeve. The invention also relates to use of the abovementioned device.

BACKGROUND OF THE INVENTION

Extraction devices of the type defined above are described in U.S. Pat. No. 4,498,468. In this prior art extraction device, an extraction handle subjects the pin to torsional forces when the pin is pulled backwards into the sleeve by turning or rotating the extraction handle. These torsional forces press the front part of the pin against one edge of the opening in the sleeve from which the front part of the pin extends. The front part of the pin is pressed against one edge of the opening during the entire drawing-in movement and until the front part of the pin is situated within the opening. It has been noticed that the front part of the pin is pressed against the edge of the opening with such power that the front part cuts into the edge or vice versa such that the front part clings to the edge. This means that there is a risk that the front part of the pin is broken or that the pin breaks at a threaded rear part since this part is weakened because of the threads. If the front part of the pin is broken, this part remains in the bone and if the pin is broken at the threaded rear part thereof, the pin can not be withdrawn or the withdrawal or extraction will at least cause some problems. These drawbacks are unacceptable when after fixation of the bone fragments, the fixation means shall be removed.

SUMMARY OF THE INVENTION

The object of the present invention is to eliminate this problem and this is arrived at by providing the device that draws the pin backwards relative to the sleeve without subjecting the pin to torsional forces.

The present invention prevents the front part of the pin from pressing against the edge of the opening in the sleeve when the pin is withdrawn or extracted into the sleeve through the opening and thus, the front part can not cling to the edges of the opening. This means that the risk of breaking the pin at the front or at the back is eliminated.

BRIEF DESCRIPTION OF THE DRAWINGS

The invention will be further described below with references to the accompanying drawings, in which:

FIG. 3 is a perspective view of an inner extraction member forming part of the device of FIG. 1;

FIG. 4 is a longitudinal section of the inner extraction member of FIG. 3;

DESCRIPTION OF EXAMPLE EMBODIMENTS

Figure 1:
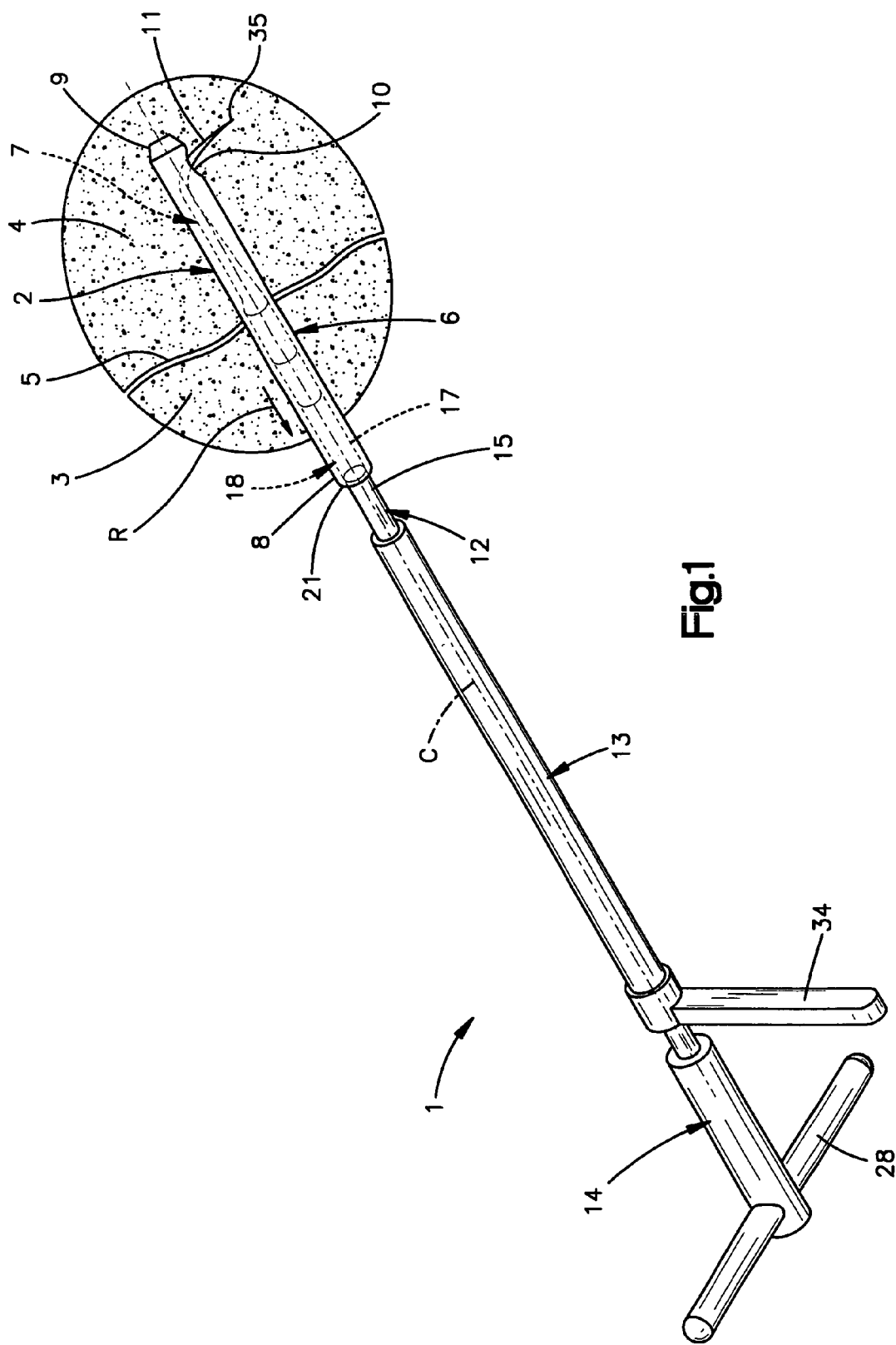
FIG. 1 is a perspective view of a device according to the invention, wherein the device is connected to a fixation means for pulling the pin thereof backwards.
Figure 2:
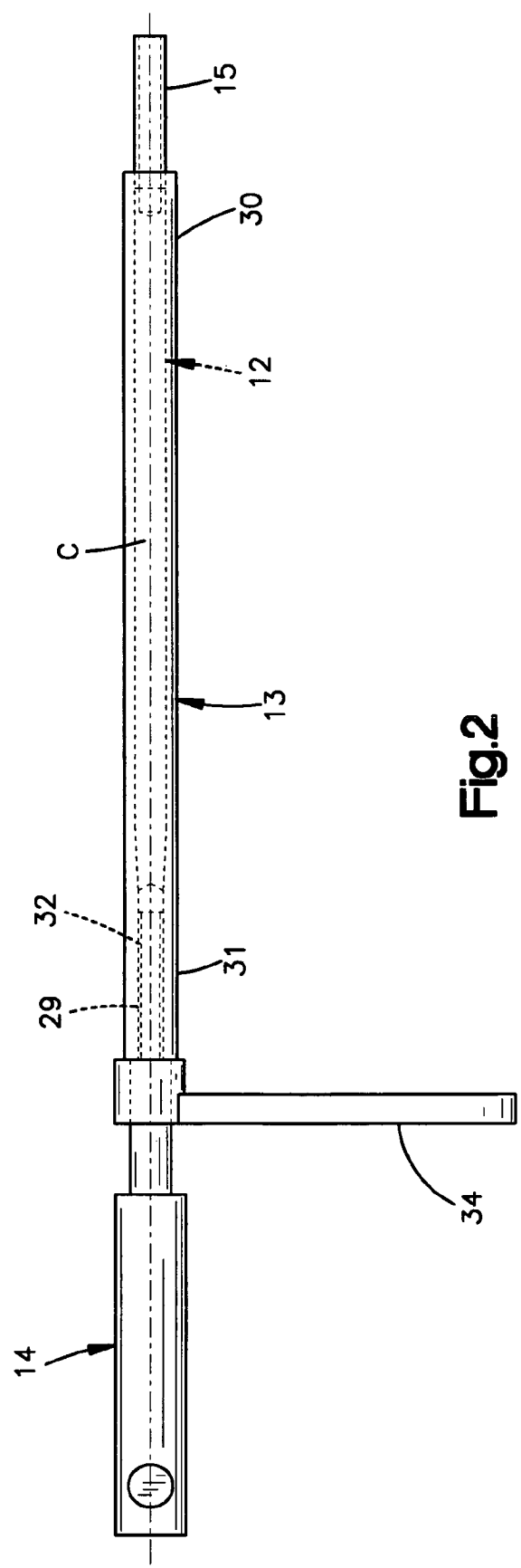
FIG. 2 is a side view of the device of FIG. 1.
Figure 5:
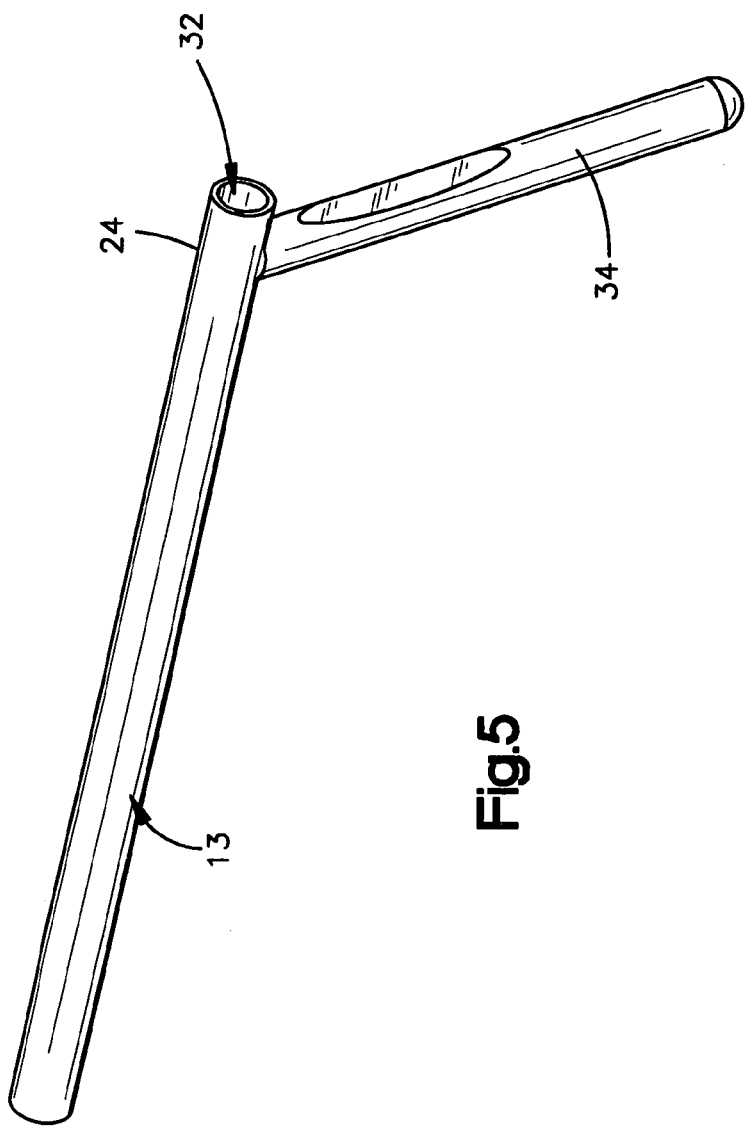
FIG. 5 is a perspective view of an outer extraction member forming part of the device of FIG. 1.
Figure 6:
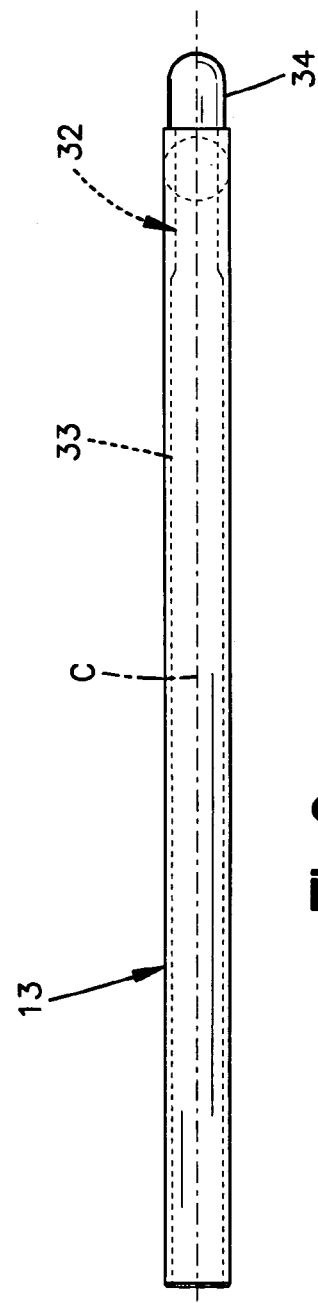
FIG. 6 is a side view of the outer extraction member of FIG. 5.
Figure 7:
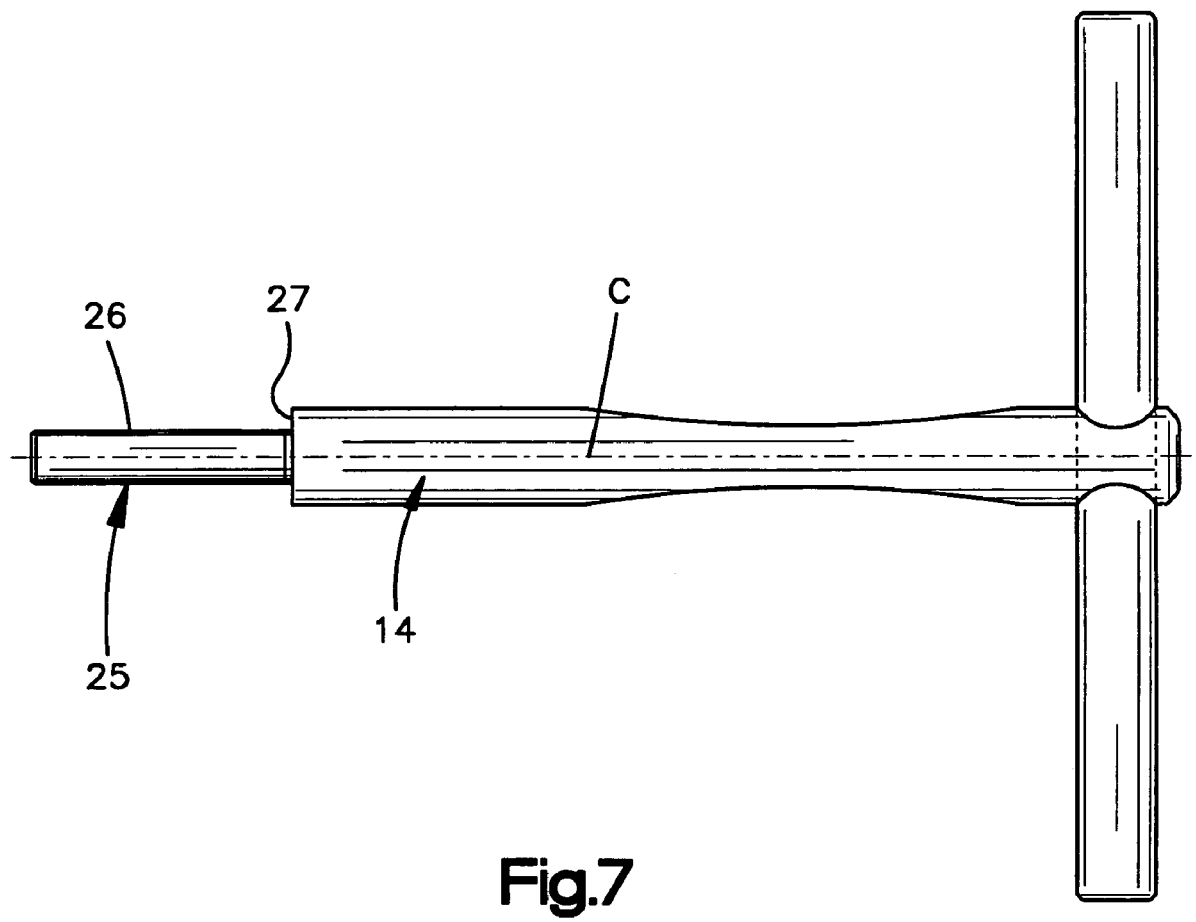
FIG. 7 is a side view of an extraction handle forming part of the device of FIG. 1.

The extraction device 1 illustrated in the drawings is adapted for extraction or withdrawal of fixation means 2 for fixation of bone fragments 3, 4 at bone fractures 5. The bone fragments 3, 4 to be fixed can be bone fragments at femoral fractures, collar bone fractures or at fractures of any other bone in the body.

The fixation means 2 may be of any prior art type—see e.g. U.S. Pat. No. 4,498,468— and it may include a sleeve 6 and at least one pin 7 provided in the sleeve 6. The sleeve 6 has an open rear end portion 8 and a front end portion 9 having at least one opening 10 in a longitudinal side of the sleeve 6 but being otherwise closed. The pin 7 can be driven into the sleeve 6 in a forward direction by means of a drawing-in instrument (already known per se and therefore not shown) such that a front part 11 of the pin 7 is brought to protrude through the opening 10 until it engages the bone material of the surrounding bone fragment 4. Thereby, the fixation means 2 fix the bone fragments 3, 4 to each other.

The extraction device 1 is adapted for withdrawal of the front part 11 of the pin 7 from the bone material of the bone fragment 4 to enable removal of the sleeve 6 when the fracture 5 is healed. To accomplish this, the extraction device 1 comprises, in the embodiment shown, three members, namely an inner extraction member 12, an outer extraction member 13 and a manually operable extraction handle 14, and these three members are provided to pull the pin 7 backwards relative to the sleeve 6 without subjecting the pin 7 to torsional forces in relation thereto. Thereby, one avoids the problem that the front part 11 of the pin 7 engages one of the edges of the opening 10 when the pin is pulled into the opening 10 so that the front part 11 of the pin 7 can not cut into the edge or vice versa so that the front part 11 does not cling to the edge.

In the embodiment shown, the inner extraction member 12 includes an elongated rod which at a front end portion 15 has an axially directed hole with inner threads 16. The front end portion 15 has such a diameter that it can be pushed into the rear end portion 8 of the sleeve 6 and its inner threads 16 mesh with outer threads 17 on a rear part 18 of the pin 7 such that the inner extraction member 12 can be screwed onto the rear part 18.

The front end portion 15 of the inner extraction member 12 transforms through an edge 19 into such portions 20 of the inner extraction member 12 which preferably have a larger diameter than the front end portion 15. The edge 19 of the inner extraction member 12 may engage a rear edge 21 of the sleeve 6 when the inner extraction member 12 is operating.

The hole with the inner threads 16 in the front end portion 15 of the inner extraction member 12 has preferably an inlet 22 without threads and tapering conically in a direction inwards into the hole. Thereby, the pin 7 can guide the inner extraction member 12 such that the inner threads 16 thereof easily "find" the outer threads 17 of the pin 7, whereby the inner and outer threads 16, 17 more easily mesh with each other in a correct manner when the inner extraction member 12 is screwed onto the pin 7. In combination with the inlet 22 without threads in the hole of the inner extraction member 12 or as an alternative thereto, an outer portion of the rear part 18 of the pin 7 may also be without threads and have a conically increasing diameter in a direction towards the outer threads 17 of the rear part 18.

The inner extraction member 12 has a hole with inner threads 23 in a rear end portion 24 and the extraction handle 14 has a front end portion 25 with outer threads 26 which fit or mesh with the inner threads 23. The front end portion 25 of the handle 14 ends at a transverse edge 27 and the extraction handle 14 has at the back a transverse handle member 28 which is engaged in order to turn or rotate the extraction handle 14.

The rear end portion 24 of the inner extraction member 12 has a rotary preventing member 29, e.g. at least an oval member 29, which can be defined by one or more flat face milled parts of the rear end portion 24 which for the rest has a circular cross section. The purpose of the rotary preventing member 29 will be described hereinafter.

The outer extraction member 13 includes, in the illustrated embodiment, an elongated sleeve which is open at a front end portion 30 as well as at a rear end portion 31. This sleeve is sized such that the inner extraction member 12 can be inserted into the sleeve and displaced in an axial extraction direction R relative to the sleeve. The rear end portion 31 of the outer extraction member 13 has inside the sleeve a rotary preventing member 32, e.g. in the form of a flat constriction of the interior of the sleeve, the rest of which has a circular cross-sectional shape.

The inner extraction member 12 can be inserted into the outer extraction member 13 so that rotary preventing members 29 of the former cooperate with the rotary preventing members 32 of the latter in such a way that they prevent rotation of the inner extraction member 12 and the pin 7 relative to the outer extraction member 13 and the sleeve 6 about a geometric centre line C which extends along the inner and outer extraction members 12, 13 and the sleeve 6 and the pin 7 when the inner extraction member 12 and the pin 7 are pulled backwards in the direction of extraction or withdrawal R.

The outer extraction member 13 has a through hole 33 with preferably the same diameter along its entire length except for the rotary preventing member 32.

The outer extraction member 13 is held fast with the hand so that it can not rotate about the centre line C and in order to facilitate this holding it may have a sideways or laterally directed handle 34, which preferably can be provided at the rear end portion 31 of the outer extraction member 13.

The lengths of the inner and outer extraction members 12, 13 and the location as well as the shape of the rotary preventing members 29, 32 are preferably chosen such that the extraction handle 14 can cooperate with the inner extraction member 12 only when said inner extraction member 12 is inserted into the outer extraction member 13 such that the rotary preventing members 29, 32 of the extraction members 12, 13 cooperate with each other.

The outer threads 26 of the extraction handle 14 have such length and/or the inner threads 23 in the rear end portion 24 of the inner extraction member 12 have such length that the extraction handle 14 can be screwed together with the inner extraction member 12 so that the pin 7 is drawn or pulled backwards so that the tip 35 of the pin 7 is situated within the opening 10 in the sleeve 6. This means that the tip 35 of the pin 7 can cooperate with a rear edge of the opening 10 and thereby pull the sleeve 6 backwards together therewith when the sleeve is withdrawn from the bone fragments 3, 4 by means of the extraction handle 14 and the extraction force of the extraction handle 14 transferred to the pin 7 through the inner extraction member 12.

The inner extraction member 12 may have lateral holes 36, 37 which extend into the holes with the inner threads 16, 23 such that the holes can be flushed clean at the lateral holes 36, 37.

The device described above can be operated as follows:

1) the inner extraction member 12 is screwed onto the pin 7 by right hand rotation, 2) the outer extraction member 13 is inserted onto the inner extraction member 12 and located such that the rotary preventing members 29, 32 of the extraction members 12, 13 cooperate with each other, 3) the extraction handle 14 is moved, through the outer extraction member 13, into the inner extraction member 12 and is screwed onto the inner extraction member by right hand rotation, 4) the extraction handle 14 is continuously rotated to the right. When the outer extraction member 13 engages the sleeve 6, the extraction handle 14 will draw or pull, through the inner extraction member 12, the pin 7 backwards relative to the sleeve 6 in the direction of extraction or withdrawal R.

The device described above is particularly suitable for use at fixation means 2 wherein the sleeve 6 and the pin 7 consists of titanium material, but may of course also be used at fixation means 2 of other materials, e.g. stainless steel.

The invention is not limited to the device described above, but may vary within the scope of the subsequent claims. Thus, the extraction handle 14 may be displaceable backwards relative to the outer extraction member 13 instead of being rotated, the rotary preventing members 29, 32 may be of a totally different type and be located in other ways than shown and described and the lengths of the various members and threads may be chosen differently than described. Instead of choosing certain lengths on the outer threads 26 of the extraction handle 14 and/or the inner threads 23 of the inner extraction member 12 for limiting the length of extraction or withdrawal of the pin 7, other types of members limiting the extraction can be provided. The opening 10 in the sleeve 6 may be round or oval or substantially round or oval and the front part 11 of the pin 7 may have a rounded side by means of which it can cooperate with front parts of the opening 10, and another side, opposite to the rounded side, which is flat or substantially flat and which can cooperate with rear parts of the opening 10.

The invention claimed is:

1. A combination of a fixation means for fixation of bone fragments at bone fractures and an extraction device for extracting the fixation means, the extraction device being removably connected to said fixation means, the fixation means comprising a sleeve and at least one pin provided in said sleeve, the extraction device comprising an inner extraction member removably connected to the pin of the fixation means, an outer extraction member removably connected to the sleeve of the fixation means, and an extraction handle that rotates relative to the outer and inner extraction members in order to extract the pin in a direction of extraction relative to the outer extraction member and the sleeve, the direction of extraction extending along a longitudinal axis of the outer extraction member, the inner extraction member being inserted into the outer extraction member and being axially movable relative to the outer extraction member, the outer extraction member being manually holdable in order to prevent the outer extraction member from rotating when the extraction handle is rotated, the outer and inner extraction members being respectively provided with rotary preventing members that directly engage one another in order to prevent the inner extraction member from rotating relative to the outer extraction member during extraction of the pin, the rotary preventing members of the outer extraction member being non-circular cross-sectional parts of a through hole in the outer extraction member, the rotary preventing members of the inner extraction member being non-circular cross-sectional parts, the rotary preventing members of the outer extraction member are provided in a rear end portion of the outer extraction member, the rotary preventing members of the inner extraction member are provided on a rear end portion of the inner extraction member, the lengths of the inner and outer extraction members and the location and shape of the rotary preventing members are chosen such that the extraction handle can cooperate with the inner extraction member in order to draw the inner extraction member backwards in the direction of extraction when the inner extraction member is inserted into the outer extraction member so that the rotary preventing members directly engage one another, and wherein a front end portion of the inner extraction member has a hole with inner threads which mesh with outer threads of the pin, and the hole of the inner extraction member has an inlet without threads, the inlet tapering conically in a direction inwards into the hole.

2. The combination according to claim 1, wherein the extraction device comprises at least one part limiting the extraction in order to ensure that the extraction handle, through the inner extraction member, draws the pin backwards relative to the sleeve so that a tip of the pin is situated in an opening of the sleeve, and thereby cooperates with a rear edge of the opening such that the pin, through said cooperation with the rear edge of the opening, draws the sleeve backwards in the direction of extraction when the sleeve is pulled out of the bone fragment by means of the extraction handle.

3. The combination according to claim 2, wherein the extraction limiting part comprises one of outer threads on the extraction handle and inner threads on the inner extraction member having such length that the length of screwing together of the extraction handle and the inner extraction member is limited.

4. The combination according to claim 1, wherein the inner extraction member has a front end portion with such outer dimensions that it can be inserted into a rear end portion of the sleeve.

5. The combination according to claim 4, wherein the front end portion of the inner extraction member, which can be inserted into a rear end portion of the sleeve, transforms into inner portions of the inner extraction member having larger outer dimensions through an edge which can engage a rear edge of the sleeve when the inner extraction member is operating.

6. The combination according to claim 1, wherein the inner extraction member is an elongated rod and has a front end portion with a hole which is provided with inner threads which mesh with outer threads on the pin, the inner extraction member has a rear end portion with a hole with inner threads which mesh with outer threads on the extraction handle, the outer extraction member is an elongated sleeve which is open at both ends, and the inner extraction member fits into the outer extraction member and is axially displaceable in relation thereto.

7. The combination according to claim 6, wherein the inner extraction member includes lateral holes which extend into the holes with the inner threads such that the holes can be flushed clean through the lateral holes.

8. The combination according to claim 1, wherein the outer extraction member has a laterally directed handle for holding the outer extraction member such that it does not rotate when the pin is drawn in the direction of extraction.

9. The combination according to claim 1, wherein the device consists of only an inner extraction member, an outer extraction member and an extraction handle.

10. The combination according to claim 1, wherein the opening in the sleeve of the fixation means is round or oval or substantially round or oval, and the front part of the pin has a rounded side by means of which it can cooperate with front parts of an opening in the sleeve, and another side, opposite to said rounded side, which is flat or substantially flat and which can cooperate with rear parts of the opening.

11. A combination of a fixation assembly, which fixes bone fragments at bone fractures and a device for extracting the fixation assembly, the fixation assembly comprising a sleeve and at least one pin provided in said sleeve, the extraction device being removably connected to said fixation assembly and comprising:

an inner extraction member removably connected to the pin of the fixation assembly;

an outer extraction member removably connected to the sleeve of the fixation assembly; and an extraction handle that rotates relative to the outer and inner extraction members in order to extract the pin in a direction of extraction relative to the outer extraction member and the sleeve, the direction of extraction extending along a longitudinal axis of the outer extraction member;

the inner extraction member being insertable into the outer extraction member and being axially movable relative to the outer extraction member, the outer extraction member being manually engageable to prevent the outer extraction member from rotating when the extraction handle is rotated, the outer and inner extraction members being provided with rotary preventing members that directly engage one another to prevent the inner extraction member from rotating relative to the outer extraction member during extraction of the pin, the rotary preventing members of the outer extraction member being non-circular cross-sectional parts of a through hole in the outer extraction member, the rotary preventing members of the inner extraction member being non-circular cross-sectional parts, wherein a front end portion of the inner extraction member has a hole with inner threads) which mesh with outer threads of the pin, and the hole of the inner extraction member has an inlet) without threads, the inlet tapering conically in a direction inwards into the hole.

12. The combination according to claim 1, wherein the rotary preventing members of the outer extraction member include at least one axially extending flat surface on the outer extraction member, the rotary preventing members) of the inner extraction member including at least one axially extending flat surface on the inner extraction member that directly engages the at least one axially extending flat surface on the outer extraction member.

13. The combination according to claim 1, wherein the rotary preventing members prevent the inner extraction member from rotating relative to the outer extraction member about a longitudinal axis of the inner extraction member in first and second opposite directions.

14. The combination according to claim 11, wherein the rotary preventing members prevent the inner extraction member from rotating relative to the outer extraction member about a longitudinal axis of the inner extraction member in first and second opposite directions.

15. The combination according to claim 1, wherein the inner extraction member directly engages the pin.

16. The combination according to claim 11, wherein the inner extraction member directly engages the pin.

17. The combination according to claim 1, wherein the extraction handle cooperates with the inner extraction member in order to draw the inner extraction member backwards relative to the outer extraction member in the direction of extraction.

18. The combination according to claim 11, wherein the extraction handle cooperates with the inner extraction member in order to draw the inner extraction member backwards relative to the outer extraction member in the direction of extraction.

* * * * *